(12) United States Patent
Reggiardo et al.

(10) Patent No.: US 7,583,190 B2
(45) Date of Patent: Sep. 1, 2009

(54) METHOD AND APPARATUS FOR PROVIDING DATA COMMUNICATION IN DATA MONITORING AND MANAGEMENT SYSTEMS

(75) Inventors: Christopher V. Reggiardo, Castro Valley, CA (US); Brad D. Etter, Bryan, TX (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 11/264,109

(22) Filed: Oct. 31, 2005

(65) Prior Publication Data

US 2009/0068954 A1 Mar. 12, 2009

(51) Int. Cl.
*G08B 1/08* (2006.01)
*A61B 5/00* (2006.01)
(52) U.S. Cl. .................. 340/539.12; 600/309
(58) Field of Classification Search .......... 340/539.1, 340/539.15, 539.12, 539.11, 870, 870.16, 340/3.3, 3.7, 500, 501, 502, 531, 3.1, 573.1, 340/3.31, 3.32, 10.1, 825.19, 286.07, 286.06, 340/870.02; 600/316–341

See application file for complete search history.

(56) References Cited

U.S. PATENT DOCUMENTS

| | | | |
|---|---|---|---|
| 2,915,579 A | 12/1959 | Mendelsohn | |
| 3,750,687 A | 8/1973 | Williams | |
| 3,843,455 A | 10/1974 | Bier | |
| 3,930,493 A | 1/1976 | Williamson | |
| 3,994,799 A | 11/1976 | Yao et al. | |
| 4,018,547 A | 4/1977 | Rogen | |
| 4,121,282 A | 10/1978 | Ohsawa | |
| 4,193,397 A | 3/1980 | Tucker et al. | |
| 4,268,173 A | 5/1981 | Barnard et al. | |
| 4,439,197 A | 3/1984 | Honda et al. | |
| 4,447,224 A | 5/1984 | DeCant, Jr. et al. | |
| 4,494,950 A | 1/1985 | Fischell | |
| 4,531,235 A | 7/1985 | Brusen | |
| 4,570,492 A | 2/1986 | Walsh | |
| 4,686,624 A | 8/1987 | Blum et al. | |
| 4,850,959 A | 7/1989 | Findl | |
| 4,851,827 A | 7/1989 | Nicholas | |
| 4,866,396 A | 9/1989 | Tamura | |
| 4,984,581 A | 1/1991 | Stice | |

(Continued)

FOREIGN PATENT DOCUMENTS

EP 0455455 11/1991

(Continued)

OTHER PUBLICATIONS

"An Electrochemical Slow Flow Meter", http://gore.ocean.washington.edu/research/slow_flow_meter.html, 2005, 3 pages.

(Continued)

*Primary Examiner*—Jennifer Mehmood
(74) *Attorney, Agent, or Firm*—Jackson & Co., LLP (57) ABSTRACT

Method and apparatus for communicating with a sealed electronic device via the electronic device's existing data ports for programming, testing configuration or diagnosis of the electronic device such as a transmitter unit for use in a data monitoring and management system such as analyte monitoring and management system is provided.

26 Claims, 6 Drawing Sheets

U.S. PATENT DOCUMENTS

| | | | |
|---|---|---|---|
| 5,004,532 A | 4/1991 | Hale et al. | |
| 5,012,667 A | 5/1991 | Kruse | |
| 5,019,974 A | 5/1991 | Beckers | |
| 5,051,880 A | 9/1991 | Harm et al. | |
| 5,079,920 A | 1/1992 | Whitehead et al. | |
| 5,081,421 A | 1/1992 | Miller et al. | |
| 5,124,661 A | 6/1992 | Zelin et al. | |
| 5,207,666 A | 5/1993 | Idriss et al. | |
| 5,211,371 A | 5/1993 | Coffee | |
| 5,211,626 A | 5/1993 | Frank et al. | |
| 5,278,997 A | 1/1994 | Martin | |
| 5,324,599 A | 6/1994 | Oyama et al. | |
| 5,325,280 A | 6/1994 | Tortola et al. | |
| 5,366,292 A | 11/1994 | Voss | |
| 5,376,070 A | 12/1994 | Purvis et al. | |
| 5,391,250 A | 2/1995 | Cheney, II et al. | |
| 5,398,681 A | 3/1995 | Kuperschmidt | |
| 5,404,585 A | 4/1995 | Vimpari et al. | |
| 5,406,301 A | 4/1995 | Ravid | |
| 5,448,992 A | 9/1995 | Kuperschmidt | |
| 5,469,025 A | 11/1995 | Kanemori et al. | |
| 5,497,772 A | 3/1996 | Schulman et al. | |
| 5,507,288 A | 4/1996 | Bocker et al. | |
| 5,517,434 A | 5/1996 | Hanson et al. | |
| 5,559,528 A | 9/1996 | Ravid | |
| 5,568,400 A | 10/1996 | Stark et al. | |
| 5,575,770 A | 11/1996 | Melsky et al. | |
| 5,604,404 A | 2/1997 | Sahara | |
| 5,622,413 A | 4/1997 | Kim et al. | |
| 5,622,482 A | 4/1997 | Lee | |
| 5,645,709 A | 7/1997 | Birch et al. | |
| 5,660,163 A | 8/1997 | Schulman et al. | |
| 5,661,643 A | 8/1997 | Blakely et al. | |
| 5,662,461 A | 9/1997 | Ono | |
| 5,671,301 A | 9/1997 | Kuperschmidt | |
| 5,695,949 A | 12/1997 | Galen et al. | |
| 5,703,928 A | 12/1997 | Galloway et al. | |
| 5,748,872 A | 5/1998 | Norman | |
| 5,759,510 A | 6/1998 | Pillai | |
| 5,774,254 A | 6/1998 | Berlin | |
| 5,790,297 A | 8/1998 | Berlin | |
| 5,791,344 A | 8/1998 | Schulman et al. | |
| 5,815,303 A | 9/1998 | Berlin | |
| 5,822,715 A | 10/1998 | Worthington et al. | |
| 5,848,990 A | 12/1998 | Cirelli et al. | |
| 5,873,026 A * | 2/1999 | Reames | 455/67.11 |
| 5,899,855 A * | 5/1999 | Brown | 600/301 |
| 5,913,833 A | 6/1999 | Elstrom et al. | |
| 5,923,512 A | 7/1999 | Brownlow et al. | |
| 6,011,486 A * | 1/2000 | Casey | 340/7.29 |
| 6,027,459 A | 2/2000 | Shain et al. | |
| 6,027,496 A | 2/2000 | Loomis et al. | |
| 6,027,692 A | 2/2000 | Galen et al. | |
| 6,041,665 A | 3/2000 | Hussain | |
| 6,059,546 A | 5/2000 | Brenan et al. | |
| 6,063,039 A | 5/2000 | Cunningham et al. | |
| 6,066,243 A | 5/2000 | Anderson et al. | |
| 6,067,017 A * | 5/2000 | Stewart et al. | 340/573.1 |
| 6,067,463 A | 5/2000 | Jeng et al. | |
| 6,071,249 A | 6/2000 | Cunningham et al. | |
| 6,071,251 A | 6/2000 | Cunningham et al. | |
| 6,073,031 A | 6/2000 | Helstab et al. | |
| 6,077,660 A | 6/2000 | Wong et al. | |
| 6,081,104 A | 6/2000 | Kern | |
| 6,085,871 A | 7/2000 | Karamata | |
| 6,093,156 A | 7/2000 | Cunningham et al. | |
| 6,129,823 A | 10/2000 | Hughes et al. | |
| 6,132,371 A | 10/2000 | Dempsey et al. | |
| 6,144,303 A * | 11/2000 | Federman | 340/573.4 |
| 6,144,922 A * | 11/2000 | Douglas et al. | 702/31 |
| 6,154,855 A | 11/2000 | Norman | |
| 6,155,992 A | 12/2000 | Henning et al. | |
| 6,157,442 A | 12/2000 | Raskas | |
| 6,160,449 A | 12/2000 | Klomsdorf et al. | |
| 6,162,202 A | 12/2000 | Sicurelli et al. | |
| 6,164,284 A | 12/2000 | Schulman et al. | |
| 6,173,160 B1 | 1/2001 | Liimatainen | |
| 6,175,752 B1 | 1/2001 | Say et al. | |
| 6,185,452 B1 | 2/2001 | Schulman et al. | |
| 6,206,841 B1 | 3/2001 | Cunningham et al. | |
| 6,208,894 B1 | 3/2001 | Schulman et al. | |
| 6,222,514 B1 | 4/2001 | DeLuca | |
| 6,242,961 B1 | 6/2001 | Liu et al. | |
| 6,245,060 B1 | 6/2001 | Loomis et al. | |
| 6,248,067 B1 | 6/2001 | Causey, III et al. | |
| 6,262,708 B1 | 7/2001 | Chu | |
| 6,278,425 B1 | 8/2001 | DeLuca | |
| 6,283,926 B1 | 9/2001 | Cunningham et al. | |
| 6,295,506 B1 | 9/2001 | Heinonen et al. | |
| 6,298,255 B1 | 10/2001 | Cordero et al. | |
| 6,306,104 B1 | 10/2001 | Cunningham et al. | |
| 6,312,888 B1 | 11/2001 | Wong et al. | |
| 6,315,721 B2 | 11/2001 | Schulman et al. | |
| 6,368,274 B1 | 4/2002 | Van Antwerp et al. | |
| 6,372,371 B1 | 4/2002 | Iarochenko et al. | |
| 6,375,344 B1 | 4/2002 | Hanson et al. | |
| 6,375,638 B2 | 4/2002 | Nason et al. | |
| 6,377,894 B1 | 4/2002 | Deweese et al. | |
| 6,381,496 B1 | 4/2002 | Meadows et al. | |
| 6,403,944 B1 | 6/2002 | MacKenzie et al. | |
| 6,408,402 B1 | 6/2002 | Norman | |
| 6,417,074 B2 | 7/2002 | Kopley et al. | |
| 6,419,642 B1 | 7/2002 | Marchitto et al. | |
| 6,425,829 B1 | 7/2002 | Julien | |
| 6,427,088 B1 | 7/2002 | Bowman, IV et al. | |
| 6,432,585 B1 | 8/2002 | Kawakami et al. | |
| 6,437,379 B2 | 8/2002 | Kopley et al. | |
| 6,438,385 B1 | 8/2002 | Heinonen et al. | |
| 6,442,413 B1 | 8/2002 | Silver | |
| 6,466,807 B1 | 10/2002 | Dobson et al. | |
| 6,471,980 B2 | 10/2002 | Sirhan et al. | |
| 6,472,991 B1 | 10/2002 | Schulman et al. | |
| 6,492,180 B2 | 12/2002 | Brown et al. | |
| 6,506,168 B1 | 1/2003 | Fathallah et al. | |
| 6,514,460 B1 | 2/2003 | Fendrock | |
| 6,514,689 B2 | 2/2003 | Han et al. | |
| 6,522,530 B2 | 2/2003 | Bang | |
| 6,526,298 B1 | 2/2003 | Khalil et al. | |
| 6,535,753 B1 | 3/2003 | Raskas | |
| 6,540,675 B2 * | 4/2003 | Aceti et al. | 600/309 |
| 6,540,891 B1 | 4/2003 | Stewart et al. | |
| 6,544,212 B2 | 4/2003 | Galley et al. | |
| 6,551,276 B1 | 4/2003 | Mann et al. | |
| 6,558,320 B1 | 5/2003 | Causey, III et al. | |
| 6,558,321 B1 | 5/2003 | Burd et al. | |
| 6,560,471 B1 | 5/2003 | Heller et al. | |
| 6,561,978 B1 | 5/2003 | Conn et al. | |
| 6,562,001 B2 | 5/2003 | Lebel et al. | |
| 6,564,105 B2 | 5/2003 | Starkweather et al. | |
| 6,564,807 B1 | 5/2003 | Schulman et al. | |
| 6,565,509 B1 | 5/2003 | Say et al. | |
| 6,565,738 B1 | 5/2003 | Henning et al. | |
| 6,569,157 B1 | 5/2003 | Shain et al. | |
| 6,571,128 B2 | 5/2003 | Lebel et al. | |
| 6,577,899 B2 | 6/2003 | Lebel et al. | |
| 6,582,393 B2 | 6/2003 | Sage, Jr. | |
| 6,585,644 B2 | 7/2003 | Lebel et al. | |
| 6,586,971 B1 | 7/2003 | Naffziger et al. | |
| 6,596,016 B1 | 7/2003 | Vreman et al. | |
| 6,600,997 B2 | 7/2003 | Deweese et al. | |
| 6,602,469 B1 | 8/2003 | Maus et al. | |
| 6,615,061 B1 | 9/2003 | Khalil et al. | |
| 6,615,074 B2 | 9/2003 | Mickle et al. | |
| 6,641,533 B2 | 11/2003 | Causey, III et al. | |

| Patent No. | Date | Inventor(s) |
|---|---|---|
| 6,648,821 B2 | 11/2003 | Lebel et al. |
| 6,650,064 B2 | 11/2003 | Guthrie et al. |
| 6,659,948 B2 | 12/2003 | Lebel et al. |
| 6,668,196 B1 | 12/2003 | Villegas et al. |
| 6,669,663 B1 | 12/2003 | Thompson |
| 6,669,669 B2 | 12/2003 | Flaherty et al. |
| 6,679,841 B2 | 1/2004 | Bojan et al. |
| 6,687,546 B2 | 2/2004 | Lebel et al. |
| 6,692,457 B2 | 2/2004 | Flaherty |
| 6,694,191 B2 | 2/2004 | Lebel et al. |
| 6,695,885 B2 | 2/2004 | Schulman et al. |
| 6,702,857 B2 | 3/2004 | Brauker et al. |
| 6,723,072 B2 | 4/2004 | Flaherty et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,752,787 B1 | 6/2004 | Causey, III et al. |
| 6,758,810 B2 | 7/2004 | Lebel et al. |
| 6,764,581 B1 | 7/2004 | Forrow et al. |
| 6,768,425 B2 | 7/2004 | Flaherty et al. |
| 6,799,861 B2 | 10/2004 | Naghi et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,818,348 B1 | 11/2004 | Venkatesan et al. |
| 6,832,114 B1 | 12/2004 | Whitehurst et al. |
| 6,833,540 B2 | 12/2004 | MacKenzie et al. |
| 6,835,553 B2 | 12/2004 | Han et al. |
| 6,837,858 B2 | 1/2005 | Cunningham et al. |
| 6,839,596 B2 | 1/2005 | Nelson et al. |
| 6,840,912 B2 | 1/2005 | Kloepfer et al. |
| 6,849,237 B2 | 2/2005 | Housefield et al. |
| 6,859,831 B1 | 2/2005 | Gelvin et al. |
| 6,862,465 B2 | 3/2005 | Shults et al. |
| 6,873,268 B2 | 3/2005 | Lebel et al. |
| 6,893,396 B2 | 5/2005 | Schulze et al. |
| 6,895,265 B2 | 5/2005 | Silver |
| 6,898,451 B2 | 5/2005 | Wuori |
| 6,904,301 B2 | 6/2005 | Raskas |
| 6,916,159 B2 | 7/2005 | Rush et al. |
| 6,922,576 B2 | 7/2005 | Raskas |
| 6,931,327 B2 | 8/2005 | Goode, Jr. et al. |
| 6,950,708 B2 | 9/2005 | Bowman, IV et al. |
| 6,958,129 B2 | 10/2005 | Galen et al. |
| 6,958,705 B2 | 10/2005 | Lebel et al. |
| 6,974,437 B2 | 12/2005 | Lebel et al. |
| 6,990,372 B2 | 1/2006 | Perron et al. |
| 6,997,911 B2 | 2/2006 | Klitmose |
| 7,003,340 B2 | 2/2006 | Say et al. |
| 7,006,858 B2 | 2/2006 | Silver et al. |
| 7,010,356 B2 | 3/2006 | Jog et al. |
| 7,020,508 B2 | 3/2006 | Stirovic et al. |
| 7,024,245 B2 | 4/2006 | Lebel et al. |
| 7,024,249 B2 | 4/2006 | Weisner et al. |
| 7,034,677 B2 * | 4/2006 | Steinthal et al. ........ 340/539.12 |
| 7,041,468 B2 | 5/2006 | Drucker et al. |
| 7,043,287 B1 | 5/2006 | Khalil et al. |
| 7,067,498 B2 | 6/2006 | Wolf et al. |
| 7,070,591 B2 | 7/2006 | Adams et al. |
| 7,072,738 B2 | 7/2006 | Bonney et al. |
| 7,074,307 B2 | 7/2006 | Simpson et al. |
| 7,077,328 B2 | 7/2006 | Krishnaswamy et al. |
| 7,079,901 B1 | 7/2006 | Loftin et al. |
| 7,081,195 B2 | 7/2006 | Simpson et al. |
| 7,083,593 B2 | 8/2006 | Stultz |
| 7,092,762 B1 | 8/2006 | Loftin et al. |
| 7,097,983 B2 | 8/2006 | Markovsky et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,123,206 B2 | 10/2006 | Hess et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,136,704 B2 | 11/2006 | Schulman |
| 7,149,581 B2 | 12/2006 | Goedeke |
| 7,153,212 B1 | 12/2006 | Karten et al. |
| 7,154,398 B2 | 12/2006 | Chen et al. |
| 7,163,511 B2 | 1/2007 | Conn et al. |
| 7,181,261 B2 | 2/2007 | Silver et al. |
| 7,186,566 B2 | 3/2007 | Qian |
| 7,186,791 B2 | 3/2007 | Bruno et al. |
| 7,192,450 B2 | 3/2007 | Brauker et al. |
| 7,198,603 B2 | 4/2007 | Penner et al. |
| 7,202,734 B1 | 4/2007 | Raab |
| 7,205,409 B2 | 4/2007 | Pei et al. |
| 7,208,119 B1 | 4/2007 | Kurtock et al. |
| 7,211,048 B1 | 5/2007 | Najafi et al. |
| 7,225,535 B2 | 6/2007 | Feldman et al. |
| 7,226,442 B2 | 6/2007 | Sheppard, Jr. et al. |
| 7,226,978 B2 | 6/2007 | Tapsak et al. |
| 7,258,666 B2 | 8/2007 | Brown |
| 7,266,400 B2 * | 9/2007 | Fine et al. ................... 600/316 |
| 7,276,029 B2 | 10/2007 | Goode, Jr. et al. |
| 7,299,080 B2 | 11/2007 | Acosta et al. |
| 7,310,544 B2 | 12/2007 | Brister et al. |
| 2001/0023095 A1 | 9/2001 | Kopley et al. |
| 2001/0024864 A1 | 9/2001 | Kopley et al. |
| 2002/0118090 A1 | 8/2002 | Park et al. |
| 2002/0193679 A1 | 12/2002 | Malave et al. |
| 2003/0023317 A1 | 1/2003 | Brauker et al. |
| 2003/0032874 A1 | 2/2003 | Rhodes et al. |
| 2003/0060765 A1 | 3/2003 | Campbell et al. |
| 2003/0078560 A1 | 4/2003 | Miller et al. |
| 2003/0107487 A1 * | 6/2003 | Korman et al. ........... 340/573.1 |
| 2003/0198558 A1 | 10/2003 | Nason et al. |
| 2003/0212346 A1 | 11/2003 | Yuzhakov et al. |
| 2003/0217966 A1 | 11/2003 | Tapsak et al. |
| 2004/0011671 A1 | 1/2004 | Shults et al. |
| 2004/0019321 A1 | 1/2004 | Sage et al. |
| 2004/0045879 A1 | 3/2004 | Shults et al. |
| 2004/0064133 A1 | 4/2004 | Miller et al. |
| 2004/0085215 A1 | 5/2004 | Moberg et al. |
| 2004/0100376 A1 * | 5/2004 | Lye et al. ................ 340/539.12 |
| 2004/0115067 A1 | 6/2004 | Rush et al. |
| 2004/0122353 A1 | 6/2004 | Shahmirian et al. |
| 2004/0132220 A1 | 7/2004 | Fish |
| 2004/0133092 A1 | 7/2004 | Kain |
| 2004/0152622 A1 | 8/2004 | Keith et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0199059 A1 | 10/2004 | Brauker et al. |
| 2004/0208780 A1 | 10/2004 | Faries, Jr. et al. |
| 2004/0263354 A1 | 12/2004 | Mann et al. |
| 2005/0009126 A1 | 1/2005 | Andrews et al. |
| 2005/0016276 A1 | 1/2005 | Guan et al. |
| 2005/0031689 A1 | 2/2005 | Shults et al. |
| 2005/0038680 A1 | 2/2005 | McMahon |
| 2005/0043598 A1 | 2/2005 | Goode, Jr. et al. |
| 2005/0051580 A1 | 3/2005 | Ramey |
| 2005/0053365 A1 | 3/2005 | Adams et al. |
| 2005/0059926 A1 | 3/2005 | Sage, Jr. et al. |
| 2005/0065464 A1 * | 3/2005 | Talbot et al. ................... 604/66 |
| 2005/0090607 A1 | 4/2005 | Tapsak et al. |
| 2005/0112169 A1 | 5/2005 | Brauker et al. |
| 2005/0143635 A1 | 6/2005 | Kamath et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |

| | | |
|---|---|---|
| 2005/0235732 A1 | 10/2005 | Rush |
| 2005/0238503 A1 | 10/2005 | Rush et al. |
| 2005/0245795 A1 | 11/2005 | Goode, Jr. et al. |
| 2005/0245799 A1 | 11/2005 | Brauker et al. |
| 2005/0249606 A1 | 11/2005 | Rush |
| 2006/0001551 A1* | 1/2006 | Kraft et al. ............. 340/870.16 |
| 2006/0015020 A1 | 1/2006 | Neale et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0166629 A1 | 7/2006 | Reggiardo |
| 2006/0222566 A1 | 10/2006 | Brauker et al. |
| 2006/0224141 A1 | 10/2006 | Rush et al. |
| 2006/0247508 A1 | 11/2006 | Fennell |
| 2006/0273759 A1 | 12/2006 | Reggiardo |
| 2007/0078323 A1 | 4/2007 | Reggiardo et al. |
| 2007/0135697 A1 | 6/2007 | Reggiardo |
| 2007/0163880 A1 | 7/2007 | Woo et al. |
| 2007/0176867 A1 | 8/2007 | Reggiardo et al. |
| 2007/0203966 A1 | 8/2007 | Brauker et al. |
| 2007/0235331 A1 | 10/2007 | Simpson et al. |

FOREIGN PATENT DOCUMENTS

| | | |
|---|---|---|
| EP | 0878707 | 11/1998 |
| EP | 0543916 | 7/2001 |
| EP | 1130638 | 9/2001 |
| EP | 1755443 | 11/2005 |
| JP | 2001-177423 | 6/2001 |
| JP | 2001-056673 | 11/2001 |
| WO | WO-02/084860 | 10/2002 |
| WO | WO-2004/028337 | 4/2004 |
| WO | WO-2004/032994 | 4/2004 |
| WO | WO-2004/061420 | 7/2004 |
| WO | WO-2005/089103 | 9/2005 |
| WO | WO-2005/101994 | 11/2005 |
| WO | WO-2006/079114 | 7/2006 |
| WO | WO-2006/102412 | 9/2006 |
| WO | WO-2006/110913 | 10/2006 |
| WO | WO-2006/113408 | 10/2006 |
| WO | WO-2006/113521 | 10/2006 |
| WO | WO-2006/118947 | 11/2006 |
| WO | WO-2006/132884 | 12/2006 |
| WO | WO-2007/041072 | 4/2007 |
| WO | WO 2007/090037 | 8/2007 |

OTHER PUBLICATIONS

Barbosa, R. M., et al., "Electrochemical Studies of Zinc in Zinc-Insulin Solution", *Journal of the Royal Society of Chemistry, Analyst*, vol. 121, No. 12, 1996, pp. 1789-1793.

Bard, A. J., et al., "Methods Involving Forced Convection—Hydrodynamic Methods", *Electrochemical Methods—Fundamentals and Applications*, 2001, pp. 331-367.

Kissinger, P. T., "Introduction to Analog Instrumentation", *Laboratory Techniques in Electroanalytical Chemistry, Second Edition, Revised and Expanded*, 1996, pp. 165-194.

Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.

* cited by examiner

METHOD AND APPARATUS FOR PROVIDING DATA COMMUNICATION IN DATA MONITORING AND MANAGEMENT SYSTEMS

BACKGROUND

Analyte, e.g., glucose, monitoring systems including continuous and discrete monitoring systems generally include a small, lightweight battery powered and microprocessor controlled system which is configured to detect signals proportional to the corresponding measured analyte levels using an electrometer, and RF signals to transmit the collected data. One aspect of certain glucose monitoring systems include a transcutaneous or subcutaneous analyte sensor configuration which is, for example, partially mounted on the skin of a subject whose glucose level is to be monitored. The sensor cell may use a two or three-electrode (work, reference and counter electrodes) configuration driven by a controlled potential (potentiostat) analog circuit connected through a contact system.

The compact size of the transmitter unit generally configured to provide water tight seals as its housing does not typically include removable components such as battery covers or additional electrical contacts that may be exposed to the environment or to the patient's skin without the addition of seals and covers. Indeed, other than the electrical contacts of the transmitter unit for coupling the sensor electrodes, the transmitter unit components and its electronic circuitry is generally sealed off from the outside elements to avoid contamination, and potential exposure to water or other fluids that may damage the transmitter unit.

In view of the foregoing, it would be desirable to have an approach to provide data communication into a sealed electronic device using existing data ports of the electronic device to communicate therewith, in the microprocessor controlled system. More specifically, it would be desirable to have a method and system for accessing the electronics of the transmitter unit (or any other sealed electronic devices) to provide programming instructions and/or otherwise configure the device using the existing data ports of the electronic device.

SUMMARY OF THE INVENTION

In view of the foregoing, in accordance with the various embodiments of the present invention, there is provided a method and apparatus for providing data communication with a sealed and encased electronic device such as a transmitter unit as used in data monitoring systems, using the existing analog electrical contacts of the transmitter units.

More specifically, in one embodiment of the present invention, there is provided an external interface unit configured to communicate with the transmitter unit electrical contacts configured for coupling to a respective one or more of the analyte sensor electrodes. For example, using an RS 232 interface circuitry, data communication via the transmitter unit electrical contacts may be achieved to program or test the electronic circuitry of the transmitter unit before the transmitter unit is initialized for use by a user in the data monitoring and management system.

DETAILED DESCRIPTION

Figure 1:
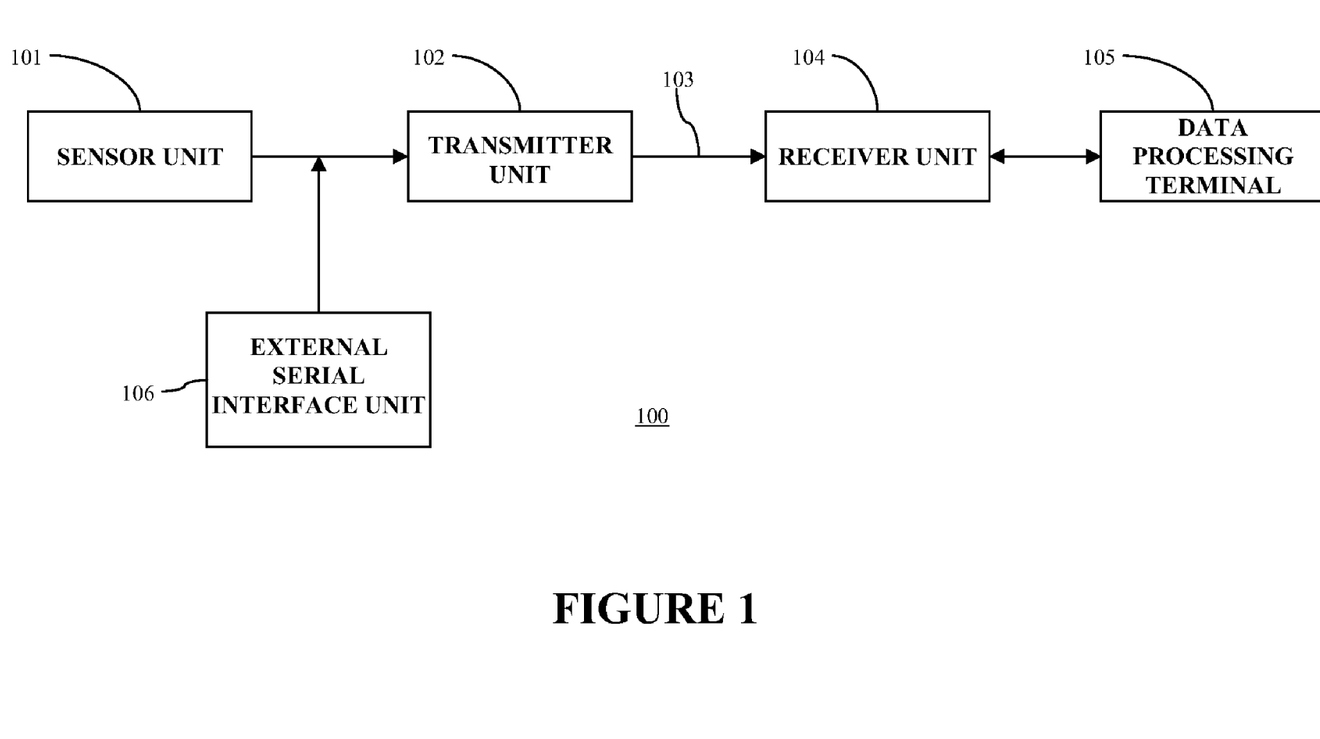
FIG. 1 illustrates a block diagram of a data monitoring and management system in accordance with one embodiment of the present invention.

FIG. 1 illustrates a data monitoring and management system such as, for example, an analyte monitoring and management system 100 in accordance with one embodiment of the present invention. In such embodiment, the analyte monitoring and management system 100 includes a sensor unit 101, a transmitter unit 102 coupled to the sensor unit 101, and a receiver unit 104 which is configured to communicate with the transmitter unit 102 via a communication link 103. The receiver unit 104 may be further configured to transmit data to a data processing terminal 105 for evaluating the data received by the receiver unit 104.

Referring to FIG. 1, also shown is an external serial interface unit 106 operatively coupled to the transmitter unit 102. In one embodiment, the external serial interface unit 106 may be configured to communicate with the transmitter unit 102 via the electrical contacts configured to couple with the sensor unit 101 electrodes. Indeed, as discussed in further detail below, in one embodiment of the present invention, data communication access to the transmitter unit 102 electronics may be achieved via the existing electrical contacts on the transmitter unit 102 such that the integrity of the transmitter unit 102 housing may be maintained.

More specifically, the external serial interface unit 106 may be configured to establish a one-way data communication to the transmitter unit 102 initially with the factory default settings, and thereafter, perform initial diagnosis, testing, and/or configuration of the transmitter unit 102 to configure the transmitter unit 102 in functional operation with the sensor unit 101, and the receiver unit 104 and/or the data processing terminal 105 in the data monitoring and management system 100. In one embodiment, the external serial interface unit 106 may be configured to establish the one way data communication to the transmitter unit 102 before the sensor unit 101 is coupled to the transmitter unit 102.

Only one sensor unit 101, transmitter unit 102, communication link 103, receiver unit 104, and data processing terminal 105 are shown in the embodiment of the analyte monitoring and management system 100 illustrated in FIG. 1. However, it will be appreciated by one of ordinary skill in the art that the analyte monitoring and management system 100 may include one or more sensor unit 101, transmitter unit 102, communication link 103, receiver unit 104, and data processing terminal 105, where each receiver unit 104 is uniquely synchronized with a respective transmitter unit 102. Moreover, within the scope of the present invention, the analyte monitoring and management system 100 may be a continuous monitoring system, or a semi-continuous or discrete monitoring system.

Indeed, analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

In one embodiment of the present invention, the sensor unit 101 is physically positioned on the body of a user whose glucose level is being monitored. The sensor unit 101 may be configured to continuously sample the glucose level of the user and convert the sampled glucose level into a corresponding data signal for transmission by the transmitter unit 102. In one embodiment, the transmitter unit 102 is mounted on the sensor unit 101 so that both devices are positioned on the user's body. The transmitter unit 102 performs data processing such as filtering and encoding on data signals, each of which corresponds to a sampled glucose level of the user, for transmission to the receiver unit 104 via the communication link 103.

In one embodiment, the analyte monitoring and management system 100 is configured as a one-way RF communication path from the transmitter unit 102 to the receiver unit 104. In such embodiment, the transmitter unit 102 may be configured to transmit the sampled data signals received from the sensor unit 101 without acknowledgement from the receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the receiver unit 104 may be configured to detect such transmitted encoded sampled data signals at predetermined time intervals.

Additionally, in one aspect, the receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the receiver unit 104 may include a data processing section which is configured to process the data signals received from the transmitter unit 102 such as by performing data decoding, error detection and correction, data clock generation, and data bit recovery.

In operation, upon completing the power-on procedure, the receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the receiver unit 104 is configured to begin receiving from the transmitter unit 102 data signals corresponding to the user's detected glucose level. More specifically, the receiver unit 104 in one embodiment is configured to perform synchronized time hopping with the corresponding synchronized transmitter unit 102 via the communication link 103 to obtain the user's detected glucose level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected glucose level of the user.

Within the scope of the present invention, the data processing terminal 105 may include an infusion device such as an insulin infusion pump, which may be configured to administer insulin to patients, and which is configured to communicate with the receiver unit 104 for receiving, among others, the measured glucose level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected glucose levels received from the transmitter unit 102.

Figure 2:
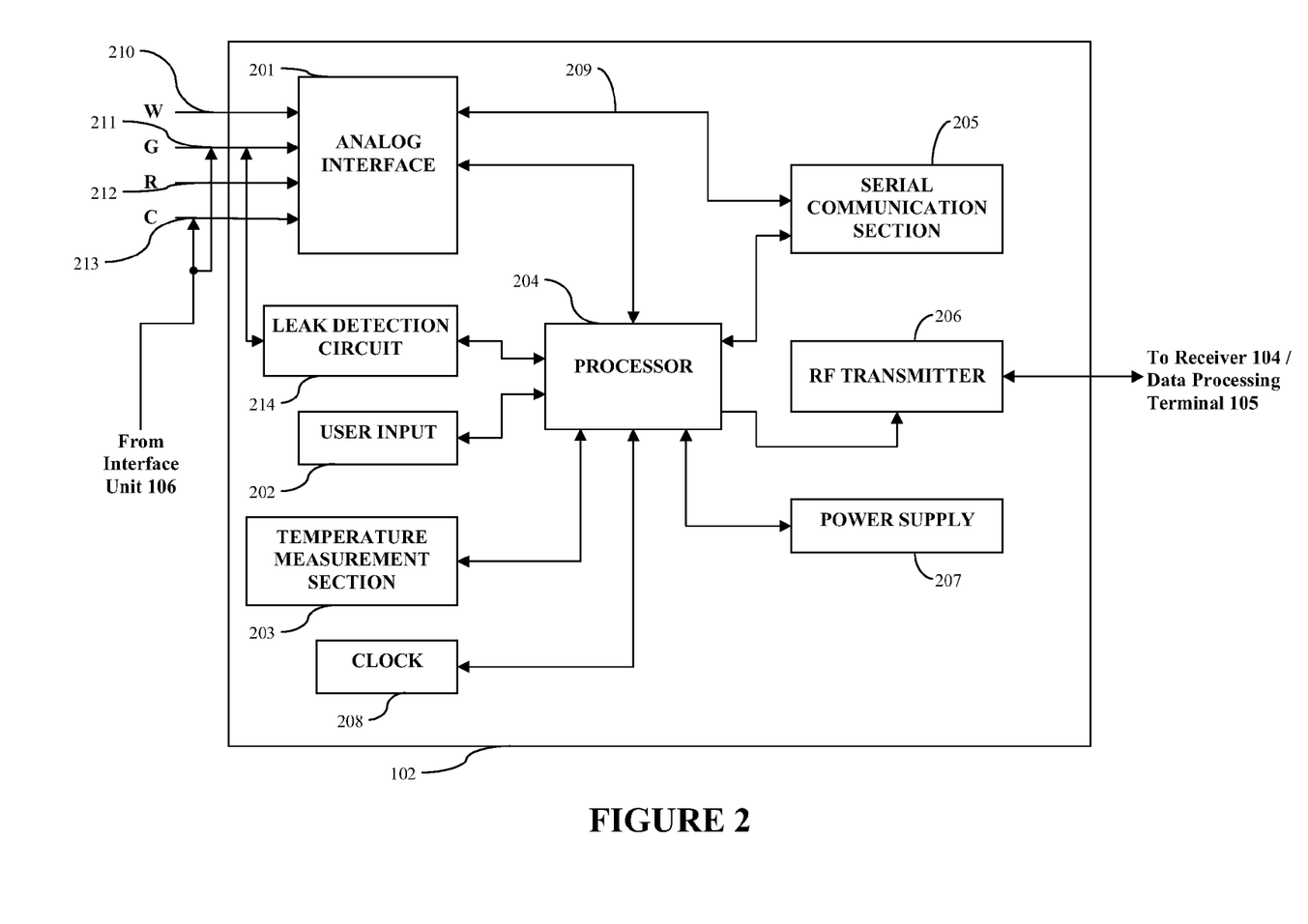
FIG. 2 is a block diagram of the transmitter unit of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter unit 102 in one embodiment includes an analog interface 201 configured to communicate with the sensor unit 101 (FIG. 1), a user input 202, and a temperature detection section 203, each of which is operatively coupled to a transmitter processor 204 such as a central processing unit (CPU).

As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the transmitter unit 102 for connection to the sensor unit 201 (FIG. 1). In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched.

In one embodiment, the external serial interface unit 106 (FIG. 1) may be operatively coupled to the transmitter unit 102 electrical contacts for the guard contact 211 and the counter electrode 213, respectively, to establish data communication with the electronics of the transmitter unit 102, and further, to perform the desired configuration and/or diagnosis procedures on the transmitter unit 102 from the manufacturer factory settings. In this manner, as will be discussed in further detail below, the external serial interface unit 106 in one embodiment of the present invention may be configured to communicate with the processor 204 of the transmitter unit 102 via the serial communication section 205, and thereafter, transmit the resulting data and/or information to, for example, the receiver unit 104 via the RF transmitter 206 of the transmitter unit 102.

Further shown in FIG. 2 are a transmitter serial communication section 205 and an RF transmitter 206, each of which is also operatively coupled to the transmitter processor 204. Moreover, a power supply 207 such as a battery, including a rechargeable battery, is also provided in the transmitter unit 102 to provide the necessary power for the transmitter unit 102 where the guard contact (G) 211 and the counter electrode (C) 213 are configured to couple to the power supply 207 through ESD clamp diodes (in the analog interface 201). Additionally, as can be seen from the Figure, clock 208 is provided to, among others, supply real time information to the transmitter processor 204.

In one embodiment, the power supply 207 may be configured to be recharged via a select pair of the plurality of electrodes 210-213 such as the guard contact 211 and counter electrode 213, when the transmitter unit 102 is not mounted to a patient and configured for periodic transmission of measured data to the receiver unit 103. As further discussed below, the power supply 207 may be coupled or docked to a battery charging station or unit during the recharge process, where the power supply 207 is recharged and, thereafter, when the transmitter unit 102 is mounted to the patient and coupled to the sensor unit 101, the power supply 207 may be configured to provide the necessary power to reliably operate the transmitter unit 102.

Referring back to the Figures, in one embodiment, a unidirectional input path is established from the sensor unit 101 (FIG. 1) and/or manufacturing and testing equipment via the external serial interface unit 106 to the analog interface 201 of the transmitter unit 102, while a unidirectional output is established from the output of the RF transmitter 206 of the transmitter unit 102 for transmission to the receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206.

As such, in one embodiment, via the data path described above, the transmitter unit 102 is configured to transmit to the receiver unit 104 (FIG. 1), via the communication link 103 (FIG. 1), processed and encoded data signals received from the sensor unit 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 may be configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor unit 101. The stored information may be retrieved and processed for transmission to the receiver unit 104 under the control of the transmitter processor 204. Furthermore, the power supply 207 may include a commercially available non-rechargeable battery or a proprietary or commercially available rechargeable battery.

The transmitter unit 102 is also configured such that the power supply section 207 does not significantly affect the battery life after having been stored for 18 months in a low-power (non-operating) mode. In one embodiment, this may be achieved by the transmitter processor 204 operating in low power modes in the non-operating state, for example, drawing no more than approximately 1 µA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved.

Referring yet again to FIG. 2, the temperature detection section 203 of the transmitter unit 102 is configured to monitor the temperature of the skin near the sensor insertion site. The temperature reading is used to adjust the glucose readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the receiver unit 104.

Additional detailed description of the continuous glucose monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application.

Figure 3:
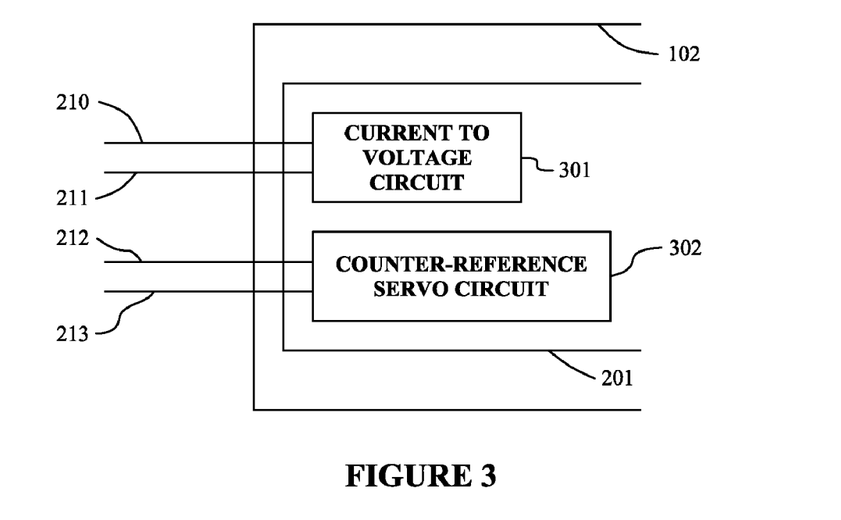
FIG. 3 illustrates the front end section of the analog interface of the transmitter unit in accordance with one embodiment of the present invention.

FIG. 3 illustrates the front end section of the analog interface of the transmitter in accordance with one embodiment of the present invention. Referring to the Figure, the front end section of the analog interface 201 includes a current to voltage circuit 301 which is configured to operatively couple to the work electrode 210 and the guard contact 211, and a counter-reference servo circuit 302 which is configured to operatively couple to the reference electrode 212 and the counter electrode 213.

Figure 4A:
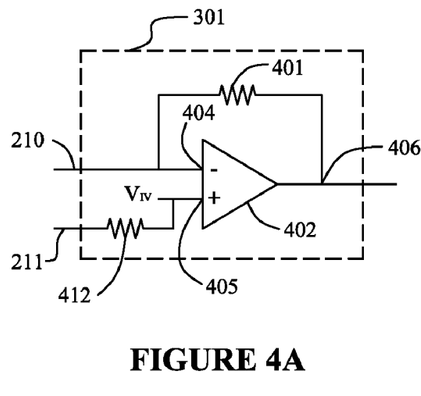
FIGS. 4A-4C respectively show detailed illustrations of the current to voltage circuit, the counter-reference servo circuit of the analog interface, and the comparator circuitry operatively coupled to the current to voltage circuit and the counter-reference servo circuit shown in FIG. 3 in accordance with one embodiment of the present invention.
Figure 4B:
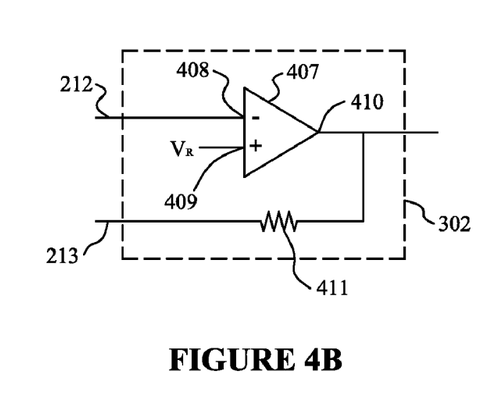
Figure 4C:
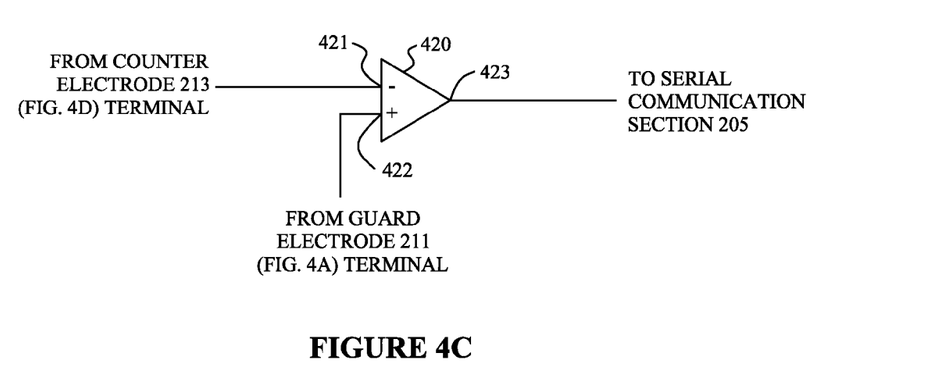

FIGS. 4A-4C respectively show detailed illustrations of the current to voltage circuit, the counter-reference servo circuit of the analog interface, and the comparator circuitry operatively coupled to the current to voltage circuit and the counter-reference servo circuit shown in FIG. 3 in accordance with one embodiment of the present invention. Referring to FIG. 4A, the current to voltage circuit 301 (FIG. 3) in one embodiment includes an operational amplifier 402 having a non-inverting input terminal 405, and an inverting input terminal 404. Also shown in the Figure is a resistor 401 operatively coupled to the inverting input terminal 404 of the operational amplifier 402, and an output terminal 406.

Referring again to FIG. 4A, the work electrode 210 is operatively coupled to the inverting input terminal 404 of the operational amplifier 402, while the guard contact 211 is operatively coupled to the non-inverting input terminal 405 of the operational amplifier 402. It can be further seen that the work voltage source Vw is provided to the non-inverting terminal 405 of the operational amplifier 402. In this manner, in accordance with one embodiment of the present invention, a separate contact, the guard contact 211 is operatively coupled to the analog interface 201 (FIG. 2) of the transmitter unit 102 (FIG. 2). The guard contact 211 is provided at a substantially equipotential to the work electrode 210 such that any current leakage path to the work electrode 210 (from either the reference electrode 212 or the counter electrode 213, for example) is protected by the guard contact 211 by maintaining the guard contact 211 at substantially the same potential as the work electrode 210.

Moreover, a resistor 412 may be provided between the guard contact 211 electrical contact (at the transmitter unit 102 analog interface unit 201) and the non-inverting input terminal 405 of the operational amplifier 402 of the current to voltage circuit 301 (FIG. 3). As will be discussed in further detail below, the resistor 412 in conjunction with a resistor coupled between the counter electrode 213 and the output terminal 410 of the operational amplifier 407 (FIG. 4B), are configured to allow serial data input on the counter electrode 213 electrical contact at the transmitter unit 102 analog interface unit 201, such that the output signal at the output terminal 410 of the operational amplifier 407 for the counter-reference servo unit 302 (FIG. 3), may be overdriven without potentially damaging the operational amplifier 407.

Referring now to FIG. 4B, the counter-reference servo unit 302 in accordance with one embodiment includes an operational amplifier 407 having an inverting input terminal 408 and a non-inverting input terminal 409, as well as an output terminal 410. In one embodiment, the reference electrode 212 is operatively coupled to the inverting input terminal 408, while the counter electrode 213 is operatively coupled to the output terminal 410 of the operational amplifier 407 in the counter-reference servo unit 302. It can also be seen from FIG. 4B that a reference voltage source Vr is provided to the non-inverting input terminal 409 of the operational amplifier 407 in the counter-reference servo unit 302.

Referring back to FIGS. 3 and 4A-4B, in accordance with one embodiment of the present invention, the current to voltage circuit 301 and the counter-reference servo unit 302 are operatively coupled to the remaining sections of the analog interface 201 of the transmitter unit 102, and configured to convert the detected glucose level at the sensor unit 101 (FIG. 1) into an analog signal for further processing in the transmitter unit 102. It should also be noted that, in the manner described, the Poise voltage (for example, at a value of 40 mV) may be determined based on the difference between the voltage signal level of the work voltage source Vw at the non-inverting input terminal 405 of the operational amplifier 402 in the current to voltage circuit 301, and the voltage signal level of the reference voltage source Vr at the non-inverting input terminal 409 of the operational amplifier 407 in the counter-reference servo unit 302.

Referring back to FIG. 4B and as discussed above, the resistor 411 is provided between the electrical contact for the counter electrode 213 at the analog interface unit 201 of the transmitter unit 102 and the output terminal 410 of the operational amplifier 407 of the counter-reference servo circuit 302. In this manner, in one embodiment of the present invention, when the external serial interface unit 106 (FIG. 1) is operatively coupled to the electrical contacts of the transmitter unit 102 for the counter electrode 213 and the guard contact 211 of the sensor unit 101 (FIG. 1), the serial data input signals from the external serial interface unit 106 may not adversely effect the operational amplifier 407 of the counter-reference servo circuit 302.

Referring now to FIG. 4C, there is provided a comparator 420 having a non-inverting input terminal 421, an inverting input terminal 422, and an output terminal 423. In one embodiment, the non-inverting input terminal 421 of the comparator 420 is configured to couple to the electrical contact for the counter electrode 213 of the transmitter unit 102 analog interface unit 201. Moreover, the inverting input terminal 422 of the comparator 420 is configured to operatively couple to the electrical contact for the guard contact 211, of the transmitter unit 102 analog interface unit 201. Finally, the output terminal 423 of the comparator 420 is configured to couple to the serial communication section 205 (FIG. 2) of the transmitter unit 102.

In one embodiment, the comparator 420 may be configured to be polarity programmable to match that of the serial communication section 205 (FIG. 2) of the transmitter unit 102.

Figure 5:
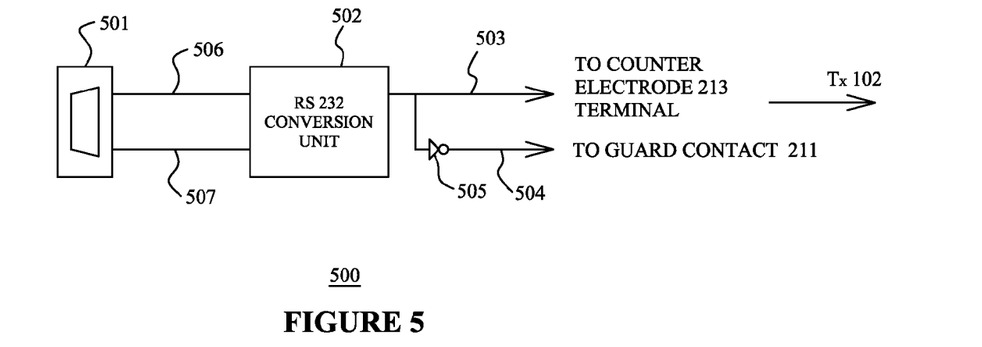
FIG. 5 illustrates an external serial interface unit for use in the data monitoring and management system in one embodiment of the present invention.

FIG. 5 illustrates an external serial interface unit for use in the data monitoring and management system in one embodiment of the present invention. Referring to FIG. 5, the external serial interface unit 500 in accordance with one embodiment includes an RS-232 data port 501 operatively coupled to an RS-232 conversion unit 502. In one embodiment, the RS-232 data port 501 may include male or female pins or sockets. Furthermore, the pin connections 506, 507 between the RS-232 data port 501 and the RS-232 conversion unit 502 may be pin #2 or #3, and the ground (pin #5) at the RS-232 data port, respectively depending upon a straight through or null-modem data transmit. The type of connectors (pins or sockets) and polarity (straight through or mull modem) may be selected using commercially available cables.

Referring back to FIG. 5, it can be seen that the RS-232 conversion unit is operatively coupled to the transmitter unit 102 analog interface unit 201 electrical contact of the counter electrode 213 via connection 503, and a logic inverter 505 is provided to drive the transmitter unit 102 analog interface unit 201 electrical contact for the guard contact 211 to establish a differential drive for signaling.

In other words, the connection 503 of the RS 232 conversion unit (FIG. 5) is operatively coupled to the non-inverting input terminal 421 of the comparator 420 (FIG. 4C), while the connection 504 of the RS 232 conversion unit (FIG. 5) is operatively coupled to the inverting input terminal 422 of the comparator 420 (FIG. 4C). This configuration allows for a differential drive signal into the transmitter unit 102 in the absence of a ground reference. The differential drive signal may be then recovered using the comparator 420 shown in FIG. 4C.

Figure 6A:
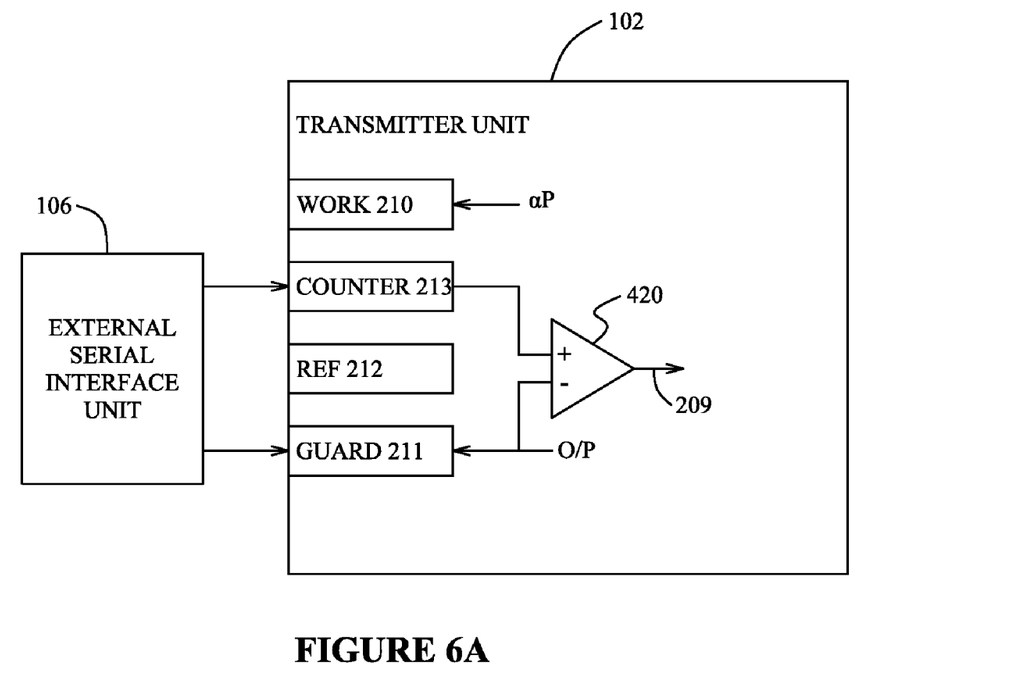
FIG. 6A is a schematic of the serial data communication in accordance with an embodiment of the present invention.
Figure 6B:
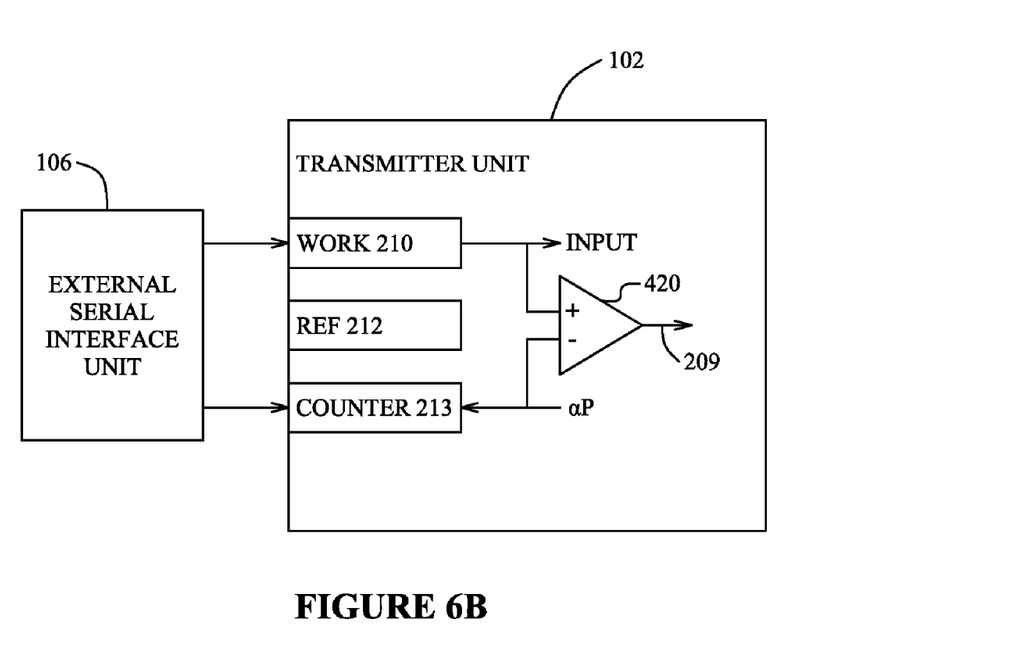
FIG. 6B is a schematic of the serial data communication in accordance with another embodiment of the present invention.

FIGS. 6A-6B are schematics of the serial data communication in accordance with various embodiments of the present invention. Referring to FIG. 6A, it can be seen that the external serial interface unit 106 (FIG. 1) is coupled to the electrical contacts for the guard contact 211 and the counter electrode 213 at the analog interface unit 201 of the transmitter unit 102. In turn, the electrical contacts for the guard contact 211 and the counter electrode 213 of the analog interface unit 201 are operatively coupled to the non-inverting input terminal 412 and the inverting input terminal 422, respectively of the comparator 420.

Referring to FIG. 6B, instead of using the electrical contact at the analog interface unit 201 of the transmitter unit for the guard contact 211, the electrical contact of the analog interface unit 201 of the transmitter unit 102 for the work electrode 210 is operatively coupled to the external serial interface unit 106 in conjunction with the electrical contact of the analog interface unit 201 of the transmitter unit 102 for the counter electrode 213. Moreover, it can be seen from FIG. 6B that the comparator 420 is provided to the transmitter unit 102 and whose non-inverting input terminal 421 and the inverting input terminal 422 are operatively coupled to the electrical contacts of the transmitter unit 102 for the work electrode 210 and the counter electrode 213.

Figure 7:
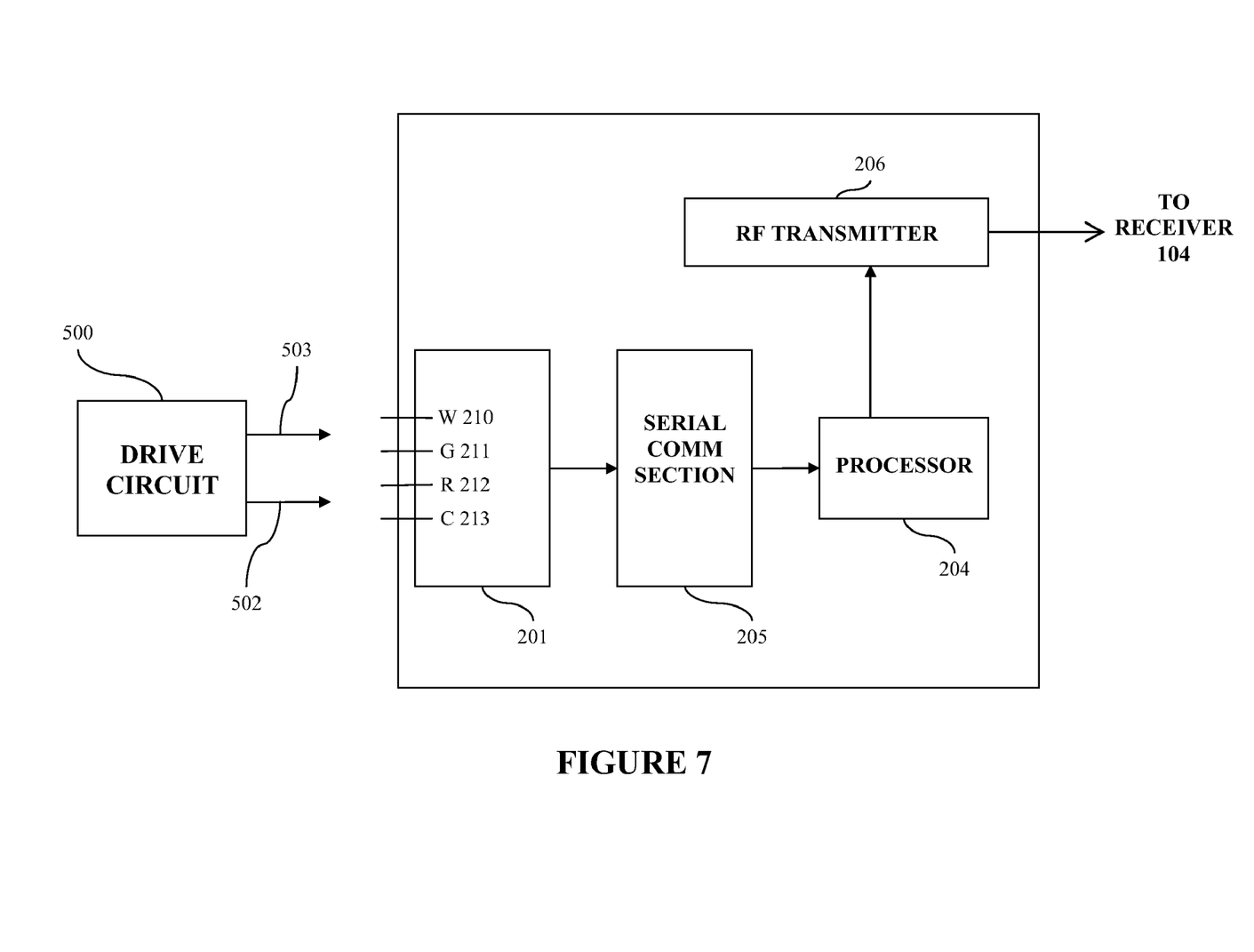
FIG. 7 illustrates a block diagram of the data flow in the data communication from the external serial interface unit and the transmitter unit in accordance with one embodiment of the present invention.

FIG. 7 illustrates a block diagram of the data flow in the data communication from the external serial interface unit and the transmitter unit in accordance with one embodiment of the present invention. Referring to FIG. 7, it can be seen that the drive circuit 500 which in one embodiment includes the external serial interface unit 106 is configured to operatively couple to the existing data ports such as the electrical contacts for coupling to the sensor unit 101 electrodes. The data signals from the drive circuit 500 are then provided to the processor 204 of the transmitter unit 102 via the serial communication section 205, and thereafter, the resulting data or information may be provided to the RF transmitter 206 to be transmit to, for example, the receiver unit 104.

In this manner, within the scope of the present invention, there is provide a method and system for communicating with an electronic device such as a transmitter unit of a data monitoring and management system provided in a substantially sealed housing for accessing the electronics of the internal circuitry of the electronic device during manufacturing, to perform for example, failure analysis, programming, calibration, boot loading, and/or for device design and testing procedures such as debug commands which may be provided to the transmitter unit in various modes to perform tests on various features.

Indeed, by providing an alternate manner in which to use existing data ports or contacts to communicate with the electronic device, substantial cost savings, complexity in design and constraint from size limitations, may be achieved. Indeed, in the case of a transmitter unit for use in the data monitoring and management system, it is possible to provide access to the transmitter unit electronics via the existing data ports or contacts, in lieu of designing the transmitter unit to include data receiver capability (for example, by providing a transceiver unit).

Accordingly, a data monitoring system in one embodiment of the present invention includes a transmitter unit including a data port, and an interface unit operatively coupled to the transmitter unit, the interface unit configured to establish a uni-directional data communication with the transmitter unit via the data port.

The transmitter unit may include a housing that is substantially water tight.

Furthermore, the transmitter unit may be configured to transmit data over a wireless data network, which includes, in one embodiment, an RF data transmission network. Indeed, the transmitter unit may include an RF transmitter.

The transmitter unit data port in one embodiment may include one or more electrical contacts configured for receiving one or more signals corresponding to an analyte level.

The system may further include a sensor unit configured to couple the data port of the transmitter unit, where the sensor unit may include an analyte sensor (such as a glucose sensor).

The sensor unit in one embodiment may be configured detect an analyte level of a patient.

A data monitoring system in another embodiment includes a transmitter unit including an input port and an output port, an interface unit operatively coupled to the transmitter unit input port, the interface unit configured to transmit signals to the transmitter unit via the input port, a receiver unit operatively coupled to the transmitter unit output port, the receiver unit configured to receive data from the transmitter unit over a data network.

The output port of the transmitter unit may include a wireless data port (such as an RF transmission data port).

In one embodiment, the interface unit may be configured to perform one or more of a transmitter unit diagnosis procedure, programming procedure, fault detection procedure, or a configuration procedure.

The interface unit may include an RS-232 interface circuit.

A method in yet another embodiment includes the steps of operatively coupling an interface unit to a data port of a transmitter unit, transmitting signals to the transmitter unit via the data port in a uni-directional path.

The method may further include the step of wirelessly transmitting data from the transmitter unit to a receiver unit, including for example, transmitting data over an RF data transmission path.

The step of transmitting signals to the transmitter unit may include the step of performing a predetermined procedure on the transmitter unit, where the predetermined procedure may include one or more of a transmitter unit diagnosis procedure, a transmitter unit programming procedure, a transmitter unit fault detection procedure, or a transmitter unit configuration procedure.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A data monitoring system, comprising:
   a transmitter unit including a data port with an electrical contact, the transmitter unit configured to operate in a first operational mode and a second operational mode; and
   an interface unit operatively coupled to the transmitter unit, the interface unit configured to establish a uni-directional data communication with the transmitter unit via the data port;
   wherein the electrical contact of the transmitter unit data port is configured for signal communication with an electrode of an analyte sensor during the first operational mode, and further wherein the electrical contact of the transmitter unit data port is configured for signal communication with the interface unit during the second operational mode.

2. The system of claim 1 wherein the transmitter unit includes a housing.

3. The system of claim 1 wherein the housing is substantially water tight.

4. The system of claim 1 wherein the transmitter unit is configured to transmit data over a wireless data network.

5. The system of claim 1 wherein the transmitter unit includes an RF transmitter.

6. The system of claim 1 wherein the electrical contact of the transmitter unit is configured to receive one or more signals corresponding to an analyte level via the data port during the first operational mode.

7. The system of claim 1 further including a sensor unit configured to couple the data port of the transmitter unit.

8. The system of claim 7 wherein the sensor unit includes an analyte sensor.

9. The system of claim 8 wherein the analyte sensor includes a glucose sensor.

10. The system of claim 7 wherein the sensor unit is configured to detect an analyte level of a patient.

11. A data monitoring system, comprising:
    a transmitter unit including a data port and an output port, the data port including an electrical contact, wherein the transmitter unit is configured to operate in a first operational mode and a second operational mode;
    an interface unit operatively coupled to the electrical contact of the transmitter unit data port, the interface unit configured to provide serial data to the transmitter unit via the electrical contact of the data port; and
    a receiver unit operatively coupled to the transmitter unit output port, the receiver unit configured to receive data from the transmitter unit over a data network;
    wherein the electrical contact of the transmitter unit data port is configured for signal communication with an electrode of an analyte sensor during the first operational mode, and further wherein the electrical contact of the transmitter unit data port is configured for signal communication with the interface unit during the second operational mode.

12. The system of claim 11 wherein the output port of the transmitter unit includes a wireless data port.

13. The system of claim 12 wherein the wireless data port includes an RF transmission data port.

14. The system of claim 11 wherein the interface unit is configured to perform one or more of a transmitter unit diagnosis procedure, programming procedure, fault detection procedure, or a configuration procedure.

15. The system of claim 11 wherein the interface unit includes an RS-232 interface circuit.

16. A method, comprising:
configuring a transmitter unit to operate in a first operational mode during a first time period and a second operational mode during a second time period;
operatively coupling an analyte sensor to the electrical contact of the transmitter unit during the first time period when the transmitter is configured to operate in the first operational mode; and
operatively coupling an interface unit to an electrical contact of the transmitter unit during the second time period when the transmitter unit is configured to operate in the second operational mode;
wherein the electrical contact of the transmitter unit is configured for signal communication with an electrode of an analyte sensor during the first operational mode, and further wherein the electrical contact of the transmitter unit is configured for signal communication with the interface unit during the second operational mode.

17. The method of claim 16 further including the step of wirelessly transmitting data from the transmitter unit to a receiver unit.

18. The method of claim 17 wherein the wirelessly transmitting step includes the step of transmitting data over an RF data transmission path.

19. The method of claim 16 wherein the step of transmitting signals to the transmitter unit includes the step of performing a predetermined procedure on the transmitter unit.

20. The method of claim 19 wherein the predetermined procedure includes one or more of a transmitter unit diagnosis procedure, a transmitter unit programming procedure, a transmitter unit fault detection procedure, or a transmitter unit configuration procedure.

21. The system of claim 1, wherein the transmitter unit is configured to receive analyte related signals from the analyte sensor via the electrical contact of the data port during the first operational mode, and further, wherein the transmitter is configured to receive an input signal from the interface unit via the electrical contact of the data port during the second operational mode.

22. The system of claim 21 wherein the received input signal from the interface unit includes a serial data input.

23. The system of claim 21 wherein the electrical contact of the data port to receive the analyte related signals during the first operational mode is the same electrical contact of the data port configured to receive the input signal from the interface unit during the second operational mode.

24. The system of claim 21 wherein the input signal received from the interface unit via the electrical contact of the transmitter unit data port during the second operational mode includes one or more of a debugging command, a reset command, a diagnosis command, or a programming command.

25. The system of claim 1 wherein the electrode of the analyte sensor includes one of a working electrode, a counter electrode, or a guard contact.

26. The system of claim 1 wherein the first operational mode and the second operational mode do not overlap.

* * * * *

UNITED STATES PATENT AND TRADEMARK OFFICE
CERTIFICATE OF CORRECTION

PATENT NO.        : 7,583,190 B2                                              Page 1 of 1
APPLICATION NO.   : 11/264109
DATED             : September 1, 2009
INVENTOR(S)       : Reggiardo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 201 days.

Signed and Sealed this

Fourteenth Day of September, 2010

David J. Kappos
*Director of the United States Patent and Trademark Office*